United States Patent
Lara Sánchez et al.

(10) Patent No.: US 11,332,709 B2
(45) Date of Patent: May 17, 2022

(54) **STRAIN OF *PSEUDOMONAS PUTIDA* AND ITS USE IN THE CONTROL OF DISEASES CAUSED BY BACTERIA AND FUNGI IN PLANTS**

(71) Applicant: FUTURECO BIOSCIENCE, S.A., Olèrdola (ES)

(72) Inventors: José Manuel Lara Sánchez, Olèrdola (ES); Carolina Fernandez Castillo, Olèrdola (ES)

(73) Assignee: FUTURECO BIOSCIENCE, S.A., Olèrdola (ES)

( * ) Notice: Subject to any disclaimer, the term of this patent is extended or adjusted under 35 U.S.C. 154(b) by 36 days.

(21) Appl. No.: 16/603,203

(22) PCT Filed: Apr. 4, 2018

(86) PCT No.: PCT/EP2018/058567
§ 371 (c)(1),
(2) Date: Oct. 4, 2019

(87) PCT Pub. No.: WO2018/185139
PCT Pub. Date: Oct. 11, 2018

(65) Prior Publication Data
US 2020/0178541 A1    Jun. 11, 2020

(30) Foreign Application Priority Data
Apr. 6, 2017 (EP) .................. 17382188

(51) Int. Cl.
*C12N 1/20* (2006.01)
*A01N 63/27* (2020.01)
*C12R 1/40* (2006.01)

(52) U.S. Cl.
CPC ............ *C12N 1/205* (2021.05); *A01N 63/27* (2020.01); *C12N 1/20* (2013.01); *C12R 2001/40* (2021.05)

(58) Field of Classification Search
None
See application file for complete search history.

(56) References Cited

FOREIGN PATENT DOCUMENTS

| EP | 1241247 A1 | 9/2002 | |
|---|---|---|---|
| WO | WO 99/05257 A1 | 2/1999 | |
| WO | WO 2013/150422 A1 | 10/2013 | |
| WO | WO-2013150422 A1 * | 10/2013 | ............. A01N 63/10 |

OTHER PUBLICATIONS

Pastor et al. 2016 (Potential of Pseudomonas putida PCI2 for the protection of tomato plants against fungal pathogens; Curr Microbiol 73:346-353 (Year: 2016).*
International Search Report and Written Opinion dated May 15, 2018 for PCT Application No. PCT/EP2018/058567, 14 pages.
Andreote, et al: "Endophytic Colonization of Potato (*Solanum tuberosum* L.) by a Novel Competent Bacterial Endophyte, *Pseudomonas putida* Strain P9, and Its Effect on Associated Bacterial Communities", Applied and Environmental Microbiology, Mar. 27, 2009, vol. 75, No. 11, pp. 3396-3406.
Mora, et al: "Antimicrobial peptide genes in *Bacillus* strains from plant environments", International Microbiology, 2011, vol. 14, pp. 213-223.
Pastor, et al: "Potential of *Pseudomonas putida* PCI2 for the Protection of Tomato Plants Against Fungal Pathogens", Current Microbiology, Springer, Boston, May 31, 2016, vol. 73, No. 3, pp. 346-353.

* cited by examiner

*Primary Examiner* — Mary Maille Lyons
(74) *Attorney, Agent, or Firm* — Squire Patton Boggs (US) LLP

(57) ABSTRACT

The present invention refers to the strain CECT8538 of *Pseudomonas putida* and mutants thereof, and the use of said strain as a pesticide in controlling plant diseases caused by fungi and bacteria. Further aspects of the invention relate to methods for preparing pesticidal compositions comprising said strain. Finally, the invention relates to a method for controlling various plant diseases caused by fungi and bacteria in a plant, comprising treating the plant and/or seed thereof or substrate used for growing said plant with the strain CECT8538 of *P. putida* or a composition including it.

16 Claims, 3 Drawing Sheets

Specification includes a Sequence Listing.

STRAIN OF PSEUDOMONAS PUTIDA AND ITS USE IN THE CONTROL OF DISEASES CAUSED BY BACTERIA AND FUNGI IN PLANTS

CROSS REFERENCE TO RELATED APPLICATIONS

This is a National Stage Application filed under 35 U.S.C. § 371 of International Application PCT/EP2018/058567 filed Apr. 4, 2018, which claims priority to EP17382188.5 filed Apr. 6, 2017, which designated the United States of America, the disclosures of each of which are incorporated herein by reference.

TECHNICAL FIELD

The present invention relates to the field of phytosanitary products, specifically to a new strain of *Pseudomonas putida* and its use in the biological control of fungal and bacterial diseases in crops of agricultural interest.

BACKGROUND ART

Nowadays, control of plant infectious diseases has focused its attention on minimizing the known impact that fungicides and bactericides have on consumer's health and the environment. For that reason, a shift to a rational use of this kind of products and an application of less toxic methods can be observed.

Although antibiotics are considered the phytosanitary products with the greatest effectiveness in controlling bacterial diseases in plants, its prolonged use favours the generation of resistant strains, which compromises its effectiveness. Moreover, the antibiotic resistance generated in these strains can be transferred to other bacteria, including human pathogens. This fact explains the ban on its use in agriculture in many countries, including the European Union. An alternative to antibiotics are broad spectrum antimicrobials such as copper-based compounds, but in this case they have limited efficacy and adverse environmental impact due to their toxicity and accumulation in the environment.

Soil-borne, non-pathogenic bacteria strains with the ability to antagonize fungal and bacterial phytopathogens have been reported in the state of the art as an alternative to chemical pesticides. However, these bacteria strains have some drawbacks. Examples of that are toxic secondary metabolites production and the lack of an appropriate ecological aptitude for plant colonisation; or certain instability over time, which makes difficult the formulation of these strains into compositions of long shelf life.

In addition to the above, in some cases it has been reported that these bacterial strains have difficulties to colonise and survive effectively in the organs of the infected host, requiring application of high concentrations or complex formulations to achieve a significant effect of disease control. Furthermore, the fact that they involve living organisms means that, although they have advantages over other synthesis pesticides, the environmental and host conditions affect their biological activity, making their effectiveness generally variable and significantly lower than the reference chemical products. Moreover, in recent years, in order to prevent the appearance of resistance in pathogenic strains for human or animals, the antibiotic-producing bacteria used as BCAs has been reduced.

In view of the above, despite the efforts made, there is still the need for bacterial strains which overcome all or part of the limitations shown by the strains already known in the state of the art in controlling plant diseases.

SUMMARY OF INVENTION

The inventors have isolated a new strain of the specie *Pseudomonas putida*, isolated from Gavá (Barcelona, Northeast of Spain), which is characterised by having a broad spectrum of activity, thus controlling various fungal and bacterial pathogens, in a wide range of soil pH.

As it is illustrated below, the strain of the invention is characterized by showing an antagonistic activity against fungal strains of *Botrytis aclada, Pythium ultimum, Rhizoctonia solani, Sclerotinia sclerotiorum, Colletotrichum coccodes, Fusarium oxysporum, Alternaria porri*, and against bacterial strain of *Erwinia carotovora* subsp. *atroseptica* (FIG. 2 and Tables 4 and 5). The present inventors have also found that the strain of the invention is able to inhibit infections caused by *Erwinia carotovora* subsp. *atroseptica* in plants under crop conditions (Table 4).

The strain of the invention presents leucine arylamidase and alkaline phosphatase activities, both having beneficious impact on plant growth, development and reproduction. Leucine arylamidase liberates amino acids from polymeric high-molecular-mass compounds providing a source of dissolved organic nitrogen that is an essential nutrient for the plant. Additionally, the alkaline phosphatase activity plays an important role in solubilization of bound phosphates, making them available to plants and also helping to its growth and development.

Regarding the biocontrol activity of the strain of the invention, as commented above, it has the capacity to antagonize different phytopathogenic agents. In this context, as illustrated in Table 5, the strain of the invention can antagonize more effectively the growth of the fungus *Botrytis aclada* than other *P. putida* strains, having a higher and long lasting effect.

Thus, it can also be concluded from the data reported below, that the effectiveness of the strain of the invention can allow its use in lower concentrations in order to reach the biocontrol activity. This may result in advantages in formulating different compositions that comprise the strain of the invention, as well as a reduction in costs related to its industrial production.

The antagonistic activity of the strain of the invention may be partly due to the expression of esterase ($C_4$) enzyme (Table 3), which has been related to biocontrol capacity due to its activity detoxifying some microbial phytotoxins, inhibiting fungal penetration into plant cells, and/or as elicitor of plant defence responses.

Despite of the high antagonistic capacity of the strain of invention, it has been surprisingly found that the strain of the invention does not express nor synthetize the antimicrobial compounds pyrrolnitrin, 2,4-diacetylphloroglucinol (2,4-DAPG), pyoluteorin and pyocyanin as described in examples 4 A and B. These metabolites are known as being the most common antimicrobial compounds produced by *Pseudomonas* spp. and are involved in the appearance of resistance in strains which are pathogenic for humans or animals. Thus, the lack of expression of these metabolites by the strain of the invention confers to it a safer profile.

Furthermore, the strain of the invention has the ability to colonise and survive in soils with pH ranging from 4 to 10 (Table 2).

The pH range of soils, can range from ultra-acidic, which are soils that have pH lower than 3.5, to very strongly alkaline soils, which have pHs higher than 9. Plants growth is dependent on micronutrients and macronutrients availability. The soil pH has a clear impact on nutrients availability. This is the reason why there are some species that can grow in some soils, and other that cannot depending on their growth requirements. On the other hand, it is well-recognized by the skilled person in the art that environment conditions such as pH can negatively affect the viability/activity of a particular microorganism. The inventors have surprisingly found that the strain of the invention can survive at very extreme pH values, between 4 and 10. That is, the effectiveness of the strain of the invention is not negatively affected by the pH of the soil, which is a further valuable advantage because it means that the strain of the invention can exert its function in any type of plant crop.

Altogether, the data provided herein allows concluding that the strain of the invention is a safe and versatile strain that can efficiently exert its action as pesticide independently of the nature of the soil, contrary to other *P. putida* strains.

Thus the present invention provides, in a first aspect, a strain of *Pseudomonas putida* deposited in the Spanish Type Culture Collection (CECT) with the access number CECT8538, or a mutant thereof, wherein said mutant strain is obtained using the CECT8538 of *Pseudomonas putida* and also maintains the following features of the starting strain: (a) antagonistic activity, and (b) the ability to colonise or survive in a part of a plant.

The strain of *Pseudomonas putida* of the invention, isolated from soil in Gavá (Barcelona, Northeast of Spain), was deposited by the applicant, according to the Budapest Treaty, on Jan. 21$^{th}$ 2014 in the Spanish Type Culture Collection (CECT), located at the University of Valencia, Edificio de Investigación, Campus de Burjassot, 46100 Burjassot, Valencia, Spain. The strain was given the access number CECT8538 after it was considered viable.

Thus, in a second aspect, the present invention provides the use of the strain CECT8538 of *P. putida* or a mutant thereof as defined in the first aspect of the invention, as a pesticide.

With regard to its use as a pesticide in plants, it is important to obtain large quantities of viable cells of the strain. As shown in Example 5, once concentrated and lyophilised, the composition shows >90% cell viability, which is maintained during storage.

In a third aspect, the present invention provides a process for obtaining a viable cell suspension derived from the strain CECT8538 of *Pseudomonas putida* or a mutant thereof as defined in the first aspect of the invention, the process comprising: (i) inoculating the strain in a culture medium, (ii) subjecting the inoculated culture medium of step (i) to conditions suitable for growth of the strain, and (iii) optionally subjecting the medium resulting from step (ii) to a concentration step.

In a fourth aspect, the present invention provides a cell-free extract derived from the strain CECT8538 of *Pseudomonas putida* or a mutant thereof as defined in the first aspect of the invention, said extract being obtainable by a process comprising: (i) inoculating the strain in a suitable culture medium; (ii) subjecting the inoculated culture medium to suitable growth conditions; (iii) separating the cells from the culture medium of step (ii); (iv) collecting the cell-free extract; and (v) optionally subjecting the cell-free extract to a concentration step.

Alternatively, once inoculated the strain and subjecting it to suitable growth conditions, the resulting inoculation product can be subjected to an inactivation step of the microorganism.

In a fifth aspect, the invention provides an inoculation product comprising the strain of the invention inactivated.

The inoculation product of the fifth aspect of the invention can exert the antagonist effect due to the secretion, during the growth step, of the metabolites responsible of that effect.

In a sixth aspect, the present invention provides a composition comprising the strain CECT8538 of *Pseudomonas putida* or a mutant thereof as defined in the first aspect of the invention, or an extract as defined in the fourth aspect, or an inoculation product as defined in the fifth aspect, and one or more agriculturally acceptable compounds.

In a seventh aspect, the present invention provides the use of the strain of the invention or a mutant thereof as defined in the first aspect of the invention, or the cell-free extract as defined in the fourth aspect of the invention, or the inoculation product as defined in the fifth aspect of the invention, or composition as defined in the sixth aspect of the invention as a pesticide.

Finally, in an eighth aspect, the present invention provides a method for controlling an infection caused by a bacterial or fungal pathogen in a plant, comprising administering the strain of the invention or a mutant thereof as defined in the first aspect, the extract as defined in the fourth aspect, the inoculation product as defined in the fifth aspect or the composition as defined in the sixth aspect, to the plant.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

In a first aspect the present invention relates a strain of *Pseudomonas putida* deposited in the Spanish Type Culture Collection (CECT) with the access number CECT8538, or a mutant thereof.

By the term "mutant" it is understood a bacterium that is obtained using, as starting material, the strain CECT8538 of

*P. putida* of the invention, and that maintains the properties of said deposited strain, concerning its antagonistic activity and the ability to colonise or survive in a part of a plant.

Figure 2:
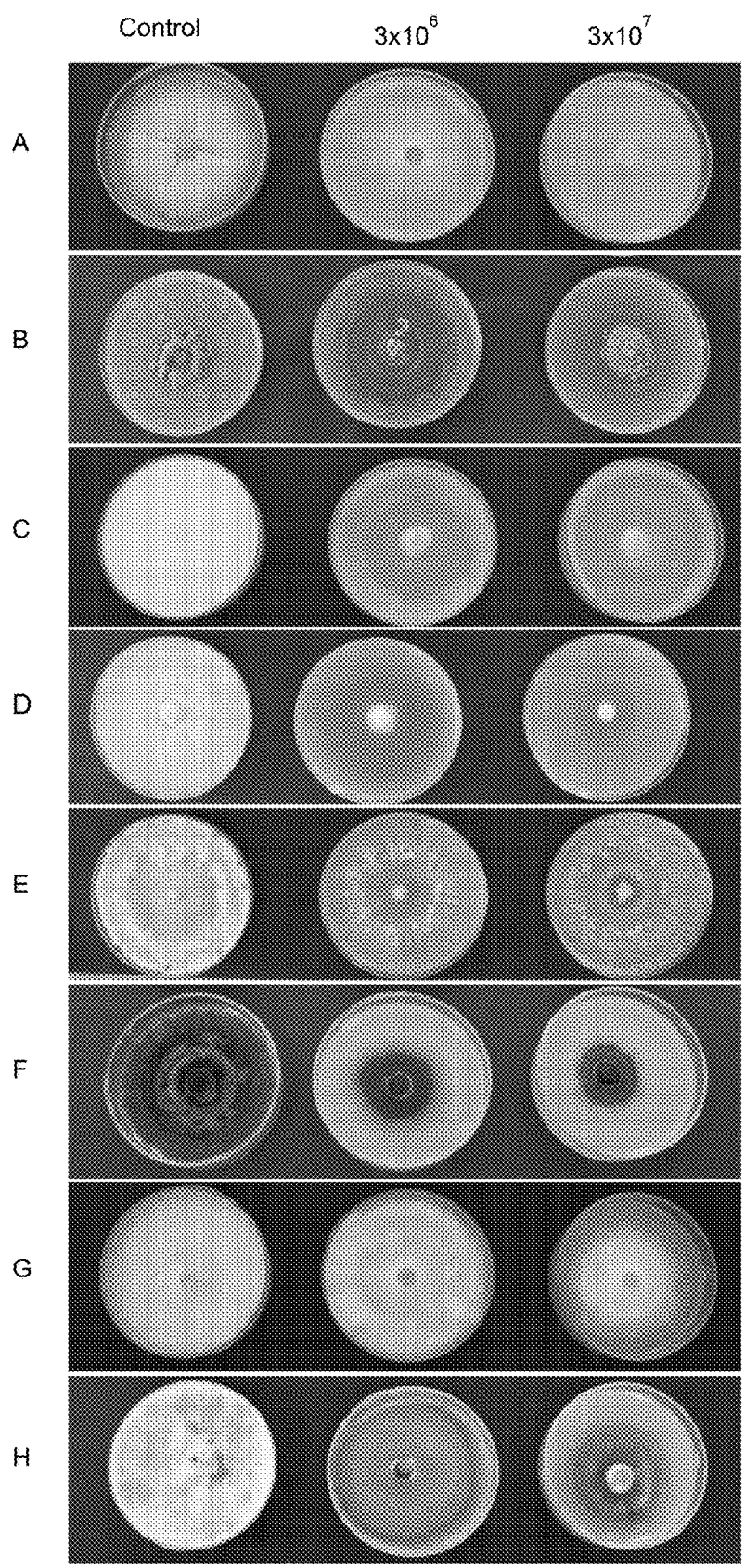
FIG. 2. CECT8538 has antifungal activity. Representative images of fitopahtogenic fungi growing on PDA containing two dosages of *P. putida* CECT8538 compared to PDA alone as a control. A: *B. aclada* CECT 2851, B: *R. solani* DSMZ 63010, C: *P. ultimum* CECT 20902, D: *S. sclerotiorum* CECT 2822, E: *S. sclerotiorum* strain H24, F: *C. coccodes* strain H827, G: *F. oxysporum* strain H828, and H: *A. porri* strain H830.

The antagonistic activity against different phytopathogens can be analysed through different methods. These methods are commonly based on the analysis of the growth capacity of the pathogens in contact with the active ingredient or the BCA, or the assessment of the severity of the disease caused by the pathogen infection after the exposition to the active ingredient or the BCA. Some routinary protocols to assess this activity are the poisoned food technique and bacterial soft rot severity analysis among others. Briefly, the poisoned food technique consists in the generation of a potato dextrose agar plate containing the biocontrol agent, the exposition of this plate to a previously prepared mycelium culture of the pathogen strains, and the assessment of the pathogenic strains growth over the time. In the case of bacterial soft severity analysis, the protocol consist in the following steps: (i) disinfection and sowing of seeds; (ii) allow seedlings growth for 4 weeks; (iii) expose the resulting plant to the pathogenic strain; (iv) incubate the plant with the biocontrol agent; and (v) assessment of the disease severity after further incubation for 4 weeks. In Examples 6 A-C below, the capacity to antagonize different phytopathogenic agents by the strain of the invention is shown. FIG. 2 and Tables 4 and 5 illustrate that the strain of the invention not only can antagonize different fungal strains more effectively than other *P. putida* strains, but also that it is effective against bacterial growth, such as *Erwinia carotovora* subsp. *atroseptica* in crop conditions.

Colonization capacity is necessary for a BCA to perform properly its function. This ability can be studied using several techniques comprising the swarming assay, or functional assays such as the assessment of the antagonistic activity under crop like conditions. For swarming motility assessment, bacterial strains are plated in specific media (M9 or BM2) plates and incubated overnight at a desired temperature. After the incubation, the multicellular bacterial surface movement is analysed. Moreover, related to the capacity to colonize, there are other capacities also involved in the adaptation to different environment conditions, such as pH and temperature tolerances. In this context, the strain of the invention shows the ability to colonize different substrates at 26° C. (FIG. 1), as well as the ability to act against bacterial infection when it is applied to the infected plant (Table 4), and it can survive in a broad range of pH, from 4-10 (Table 2).

A "mutant" of CECT8538 of *P. putida* is also understood according to the invention as a "variant" of CECT8538 of *P. putida*. The skilled in the art will understand that mutants retaining the characteristics and relevant advantages described herein can be obtained routinely, for example by spontaneous mutagenesis or directed mutation, using the strain of the invention as starting material. Methods for obtaining mutants of a specific bacterial strain are known in the art. An example can be found in Sambrook, J. and Russell, D. W. "Molecular Cloning: A Laboratory Manual", Chapter 13, "Mutagenesis", Cold Spring Harbor, 3rd Ed, 2001.

From now on, when reference is made in the present invention to the expression "strain of the invention", it encompasses the *P. putida* strain CECT8538 and the mutants thereof.

The plant may be a tuber, such as potatoes, or a tree, in particular, a fruit tree, such as a pear tree, tomato, cauliflower or pepper, among others.

Thus, the terms "pest control", and "biological pest control" are used herein interchangeably and refer to integrated pest control.

In view of the above, in another aspect, the invention refers to the use of the strain CECT8538 of *P. putida* or a mutant thereof, as a pesticide in plants.

In the present invention, the term "pesticide" is understood by its usual meaning in the field of agronomy as a product intended to kill, repel, regulate or disrupt the growth of living organisms that are considered pests. Clearly, due to the nature of the strain CECT8538 of *P. putida* or mutant thereof, herein it is understood that "pesticide" is a biological or ecological (organic) pesticide, also called biopesticide. In the scope of the present invention, the term "pesticide" would have the same meaning as the term "phytosanitary".

In the present invention, the term "control of the disease" means that it prevents, reduces, cures or eradicates the disease.

In an embodiment of the second aspect of the invention, the strain is used in preventing infections caused by bacteria or fungi in plants.

In a third aspect, the present invention relates to a process for obtaining a viable cell suspension derived from the strain of the invention comprising: (i) inoculating the strain of the invention in a suitable culture medium, (ii) subjecting the inoculated culture medium of step (i) to appropriate conditions to the growth of the strain, and (iii) optionally subjecting the medium resulting from step (ii) to a concentration step.

The term "derived from the strain of the invention" means that the suspension is obtained from the strain object of the present invention.

The strain of the invention may be inoculated in the culture medium at a final concentration comprised from 5 to 7% v/v. Preferably the inoculated culture is in an exponential growth phase. Cell growth will slow on achieving, preferably, a cell concentration comprised from $1.0 \times 10^9$ to $1.0 \times 10^{10}$ CFU/mL. Suitable culture media for the growth of the strain of the invention are synthetic media, such as LB (lysogenic broth) and PM (saline production medium), or media of plant origin such as molasses (e.g. from sugar cane, beets and others). Suitable conditions for strain's growth are temperatures comprised from 25 to 35° C., pH comprised 6 to 8, and oxygen concentration comprised from 50 to 100%. The growth of the strain of the invention is produced by stirring. An example of the detailed method for obtaining cells from the strain of the invention is reflected in Example 5.

In another embodiment of the process for obtaining the suspension, cells are separated from the medium to obtain a concentrated suspension. Suitable separation techniques include centrifugation or filtration of the culture. Carrying out the centrifugation of the culture, for example, at a minimum of 5000 rpm, cells are obtained in the pellet, which are resuspended in part of the culture medium or in a suitable buffered medium such that the strain concentration is approximately about $1 \times 10^{11}$ CFU/mL.

Once the suspension is obtained, it may be subjected to a dehydration step. Dehydration can be carried out through a lyophilisation process. Alternatively, the suspension can be dehydrated by fluidised bed drying. Another option is to dehydrate the suspension by spray drying or drying in an oven under vacuum In this regard, another advantageous feature of the strain of the invention is that it exhibits high resistance to dehydrating processes, which are routine in obtaining microorganisms on an industrial scale. In order to improve cell viability, an inert osmotic protector ingredient can be added to the suspension before carrying out the dehydration process.

In another particular embodiment of the third aspect of the invention, the process comprises resuspending the cells resulting from the separation step in a suitable buffer to yield a cell concentrated suspension.

In a fourth aspect, the present invention provides a cell-free extract derived from the strain CECT8538 of *P. putida* or a mutant thereof as defined in the first aspect of the invention, said extract being obtainable by a process comprising: (i) inoculating the strain in a suitable culture medium; (ii) subjecting the inoculated culture medium to suitable growth conditions; (iii) separating the cells from the culture medium of step (ii); (iv) collecting the cell-free extract; and (v) optionally subjecting the cell-free extract to a concentration step.

The cell-free medium obtained by the separation processes described above, could be used and/or introduced to an appropriated formulation directly or subjected to a concentration step to reach a more suitable composition. Thus, in an embodiment of the fourth aspect, the invention relates different protocols to concentrate the cell-free extract that can be used, such as dehydration, filtration, ultra-filtration, centrifugation, ultra-centrifugation, precipitation, or chromatography.

In another aspect of the invention, the invention provides in a fifth aspect an inoculation product comprising the strain of the invention.

By "inoculation product" it is understood a product obtained after inoculating the strain in a suitable culture medium, subjecting the inoculated culture medium to suitable growth conditions.

In one embodiment of the fifth aspect of the invention, the inoculation product is in a concentrated form. In another embodiment, the inoculation product is in a dried-concentrated form. Techniques for concentrating and drying the inoculation product are routine and have been provided above.

In another embodiment of the fifth aspect of the invention, the inoculation product comprises the strain of the invention inactivated.

By "inoculation product comprising the strain of the invention inactivated" refers to a product obtained after inoculating the strain in a suitable culture medium, subjecting the inoculated culture medium to suitable growth conditions, and then inactivating the strain. The term "inactivated" means that the micro-organism is not able to form colonies. In one embodiment, the inactivated micro-organisms have the cell membrane intact or broken.

In a sixth aspect, the present invention provides a composition comprising the strain as defined in the first aspect of the invention, an extract as defined in the fourth aspect, or an inoculation product as defined in the fifth aspect, and one or more agriculturally acceptable compounds.

With a view to practical use in pest control, pesticide agents are usually formulated into compositions also including suitable additives for agricultural use. The compositions of the invention may be solid (including, for example, dehydrated bacteria concentrate) or liquid (including bacteria concentrated suspensions).

"Agriculturally acceptable compounds" refers to those compounds and/or materials, which are suitable for use in agriculture. In general, said compounds should be non-toxic to humans and preferably should be environment-friendly.

In a particular embodiment of the sixth aspect of the invention, the pesticidal compositions of the invention may contain compounds for improving the adhesion of the strains in the plants to be treated, as well as phytostrengthener compounds, nutrients, wetting agents, stabilizers, osmotic protectors, antioxidants, sunscreens, buffering compounds or combinations thereof.

In another embodiment of the sixth aspect of the invention, examples of adhesion products are gelatin, starch, pectins, alginates and various types of gums such as xanthan. Many of these compounds are also wetting agents. In the case of sunscreens, Congo red, calcium carbonate and wax emulsions can be used. The phytostrengtheners are compounds that can facilitate make crops develop robustness or tolerance towards pathogens or adverse environmental conditions, for example, jasmonic acid analogues and some plant defense stimulants such as harpins, chitosans, and laminarins. Additionally, examples of osmotic protectors are trehalose, betaines and amino acids. Finally, ascorbic acid and glutathione are included among antioxidants.

In a further embodiment of the sixth aspect of the invention, the composition comprises at least one additional pesticidal agent, said additional pesticide not adversely affecting the activity of the strain CECT8538. In another embodiment of the sixth aspect of the invention, the additional pesticidal agent is selected from the group consisting of a bacterial strain effective in controlling a bacterial or fungal infection, a fungicide, a bactericide, an herbicide, an insecticide or a nematicide.

The compositions of the sixth aspect of the invention can be prepared by routine protocols, such as mixing of the different ingredients.

In a seventh aspect, the invention directs to the use of the strain of the invention as defined in the first aspect of the invention, or the cell-free extract as defined in the fourth aspect of the invention, or the inoculation product as defined in the fifth aspect of the invention, or the compositions as defined in the sixth aspect of the invention as a pesticide in plants.

In an embodiment of the seventh aspect of the invention, the invention refers to the use of the compositions of the sixth aspect to control diseases caused by fungal or bacterial pathogens in plants.

In another aspect, the invention provides a method comprising administering the strain of the invention or the mutants thereof as defined in the first aspect, or the cell-free extract as defined in the fourth aspect, or the inoculation product defined in the fifth aspect, or the compositions defined in the sixth aspect, to the affected part of the plant and/or the seed, or to the substrate or soil used for growing of said plant, for preventing, curing, reducing or eradicating a disease caused by bacterial or fungal infection.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention.

The following examples are provided by way of illustration, and they are not intended to be limiting of the present invention. Furthermore, the present invention covers all possible combinations of particular and preferred embodiments described herein.

EXAMPLES

Example 1. Isolation and Identification of *Pseudomonas putida* Strain CECT8538

In order to obtain the isolates, samples of soil collected from Spain region All samples were from fields and natural environment of Mediterranean climate. The samples were processed by conventional microbiological methods (Mora et al., "Antimicrobial peptide genes in *Bacillus* strains from plant environments", International Microbiology, 2011, vol. 14, pp. 213-223), and bacteria of the genus *Pseudomonas* were isolated in NA medium at 28° C. for 24 h, forming a collection of 2.400 isolates. CECT8538 was initially identified by 16S rDNA sequencing. 16S rDNA was amplified using the bacterial forward primer 8f, with the sequence SEQ ID NO:1 (forward primer 8f: AGTTT-GATCCTGGCTCAG), and the universal reverse-complementary primer 1492r, with SEQ ID NO:2 (reverse primer 1492r: ACGGTTACCTTGTTACGACTT), using colony PCR (a single colony from a solid culture in NA was picked with an sterile pipette tip; the tip was dipped in 50 µL sterile water, boiled for 10 min at 98° C., and placed immediately on ice until use as PCR template) with a high fidelity DNA polymerase (Biotaq, Bioline, London, UK) following manufacturer's instructions. The amplicon SEQ ID NO:3 (corresponding to the subunit 16S rDNA of the strain of the invention CECT8538) was purified and sequenced using the 8f primer. The sequence was then submitted to BLASTn homology search against the whole NCBI nucleotide database. On the basis of the 16S rDNA nucleotide sequence the bacterial isolate was initially identified as a *Pseudomonas* sp. strain closely related to the so-called "*P. putida* complex" (*P. putida/plecoglossicida/taiwanensis*).

For a more accurate identification of the bacterial strain the rpoD and gyrB nucleotide sequences, which are reported to be more discriminating within this genus, were retrieved from the whole genome shotgun sequence (WGS) and analyzed as for the 16S except that the target database was limited to *Pseudomonas* spp. entries (taxid:286). The rpoD (SEQ ID:4) and gyrB (SEQ ID:5) nucleotide sequences show that CECT8538 is a *P. putida* strain belonging to *P. putida* biovar A or C. As opposed to biovar C, biovar A *P. putida* strains are unable to grow at 4° C. Since CECT8538 was not able to grow at 4° C., it was concluded that it was a biovar A *P. putida* strain.

To obtain extensive information about the strain of the invention, including an accurate classification, a whole genome sequencing experiment was performed. For this, DNA was obtained from a CECT8538 liquid culture and sequenced using the Illumina technology (HiSeq2500) on a Nextera® DNA Library (Illumina, Cambridge, UK) following manufacturer's specifications. The data generated were analyzed by Sequentia Biotech (Barcelona, Spain) by applying a proprietary workflow, RECONSTRUCTOR, which generates an annotated whole genome shotgun (WGS) sequence using a combined de-novo and reference-assisted assembly approach. *P. putida* KT2440 (accession nr. NC_002947.4; DSM6125) was used as the reference for the reference-assisted assembly.

The WGS sequence was annotated using RAST. For the screening of rRNA operons the online tool WebMGA was used (http://weizhong-lab.ucsd.edu/metagenomic-analysis/). For the identification of tRNAs ARAGORN v1.2.36 was used. The oriC and related sequences were identified using Ori-Finder and the DoriC database. Genomic islands were identified using IslandViewer 3.

The assembly of the CECT8538 genome sequence resulted in 186 scaffolds, containing 6315656 nucleotides, built from contigs with either no BLAST hit (e-val. cut-off 0.01) or best BLAST hits in *Pseudomonas* spp. From the 186 scaffolds, the first one (herein referred to as "the chromosome") includes 5860165 bases, i.e. 92.8% of all bases sequenced. The overall GC content of the CECT8538 genome is 61.7%. IslandViewer predicts 12 genomic islands (GIs) in the chromosome, some of them matching GC-skewed regions, from which at least 5 bear prophage-related sequences. One of these GIs spans about 700 kbp and includes over 600 CDSs.

Only a fragment of a 5S rDNA copy is assembled in the CECT8538 chromosome. The entire 16S and 23S sequences, adjacent to a fragment of the 5S, are encoded in one of the largest scaffolds (excl. the chromosome). In addition, other scaffolds contain either a fragment or the entire 5S sequence each. Most likely, RECONSTRUCTOR aligns the rDNA copies with one another considering that they are overlapping reads. The CECT8538 WGS includes sequences encoding for 67 tRNAs. From these, 57 are encoded in the chromosome, and include tRNAs for 22 aminoacids, including seC (selenocysteine) and an ambiguous tRNA (for seC or Val). The oriC sequence of the CECT8538 genome comprises 573 nucleotides, flanked by the rpmH and dnaA genes, and comprises 4 dnaA boxes and two additional sequences with 1 and 2 unmatched sites, respectively.

The RAST annotation tool predicted 5892 CDSs encoded in 5595813 nucleotides (i.e. the coding regions cover 88.6% of the genome), with the CDS length ranging from 60 to 14394 nucleotides, mean and median CDS lengths of 950 and 819 nucleotides, respectively, and N50 CDS length of 1197 nucleotides. From all the CDSs, 50% were classified as hypothetical proteins.

In addition, Sequentia Biotech performed a variant calling analysis to unravel single nucleotide polymorphisms (SNPs), small insertion or deletions (INDELs) and large structural variants (SVs) in CECT8538 as compared to the reference genome (KT2440; DSM6125). After filtering by variant quality and genotype depth, CECT8538 shows 112931 SNPs and 867 INDELs (332 small deletions and 535 small insertions) as compared to KT2440. In addition, from all the CECT8538 reads obtained in the experiment, 22.3% did not map to the KT2440 genome. These reads were de novo assembled and from the assembled scaffolds 512 ORFs were predicted, including 402 complete proteins. The megablast algorithm, with default settings, did not show significant alignment with any nucleotide sequence in the NCBI database for over 200 of these ORFs, indicating that CECT8538 is not only different to the KT2440, but also from other strains.

Example 2. Characterization of Physicochemical Properties of the *Pseudomonas putida* Strain CECT8538

For the characterization assays the strain of the invention was plated in commercial nutrient agar (NA, Scharlab), M9 (0.5% Casamino Acids, 2 mM $MgSO_4$, 0.1 mM $CaCl_2$ supplemented with 0.4% glucose and solidified with 0.5% agar) or BM2 (62 mM potassium phosphate buffer, pH=7.2 mM $MgSO_4$, 10 µM $FeSO_4$, 0.5% [wt/vol] casamino acids, supplemented with glucose 0.4% and solidified with 0.5% agar)media plates. Plates were prepared after sterilization of media and once the media was cool enough, it was poured into the plates and left until it become semi-solid. For temperature profile assessment, the strain of the invention was plated in NA plates at a $10^8$ concentration (CFUs $ml^{-1}$), and incubated at different temperatures (i.e. 4° C., 26° C., 37° C. and 42° C.) for 5 days. Temperatures of 26° C. and 37° C. were found optimum for the growth of the isolate CECT8538 while it did not grow at 4° C. and 42° C. after 24 h incubation (see Table 1). As described above, CECT8538 was clustering as *P. putida* biovar A or C based on the rpoD and gyrB nucleotide sequences. Contrary to biovar C, the ability of *P. putida* biovar A strains to growth at 4° C. is relatively rare, supporting that the strain of the invention belongs to biovar A.

The antibiotic sensitivity was determined by incorporating 15 μg/ml of nalidixic acid, 50 μg/ml of chloramphenicol, 50 μg/ml of streptomycin sulfate, 50 μg/ml of oxytetracicline, or 50 μg/ml of nitrofurantoin in NA medium. Also the ability to grow in NA containing 5% of NaCl was determined. In all conditions the plates were incubated 48 h at 26° C. *P. putida* CECT8538 was resistant to 15 μg/ml of nalidixic acid and 50 μg/ml of chloramphenicol. However, the strain of the invention was not able to growth in NA containing 50 μg/ml of streptomycin sulfate, 50 μg/ml of oxytetracycline, or 5% NaCl. The antibiotic nitrofurantoin showed a lightly effect on the bacterium growth at 50 μg/ml (see Table 1).

To further characterize the strain of the invention, enzymatic activities were analyzed with an API ZYM kit according to the procedures described by the manufacturer (Bio-Mérieux, Lyon, France). The strain of the invention exhibited the enzymatic activities of esterase ($C_4$), leucine arylamidase and alkaline phosphatase.

TABLE 1

Physicochemical characteristics of *P. putida* CECT8538

| Characteristic | Result [a] |
|---|---|
| Growth at different temperatures: | |
| 4° C. | − |
| 26° C. | + |
| 37° C. | + |
| 42° C. | − |
| Growth on NA + 5% NaCl | − |
| Antibiotic resistance: | |
| Nalidixic acid (15 μg/ml) | + |
| Chloramphenicol (50 μg/ml) | + |
| Streptomycin sulfate (50 μg/ml) | − |
| Oxytetracycline (50 μg/ml) | − |
| Nitrofurantoin (50 μg/ml) | w |
| API ZYM: | |
| Alkaline phosphatase | + |
| Esterase ($C_4$) | + |
| Esterase lipase ($C_8$) | − |
| Lipase ($C_{14}$) | − |
| Leucine arylamidase | + |
| Valine arylamidase | − |
| Crystine arylamidase | − |
| Trypsin | − |
| α-Chymotrypsin | − |
| Acid phosphatase | − |
| Naphtol-AS-BI-phosphohydrolase | − |
| α-Galactosidase | − |
| β-Galactosidase | − |
| β-Glucuronidase | − |
| α-Glucosidase | − |
| β-Glucosidase | − |
| N-Acetyl-β-glucosamidase | − |
| α-Mannosidase | − |
| α-Fucosidase | − |

[a] (−) negative; (+) positive, (w) weakly positive

Figure 1:
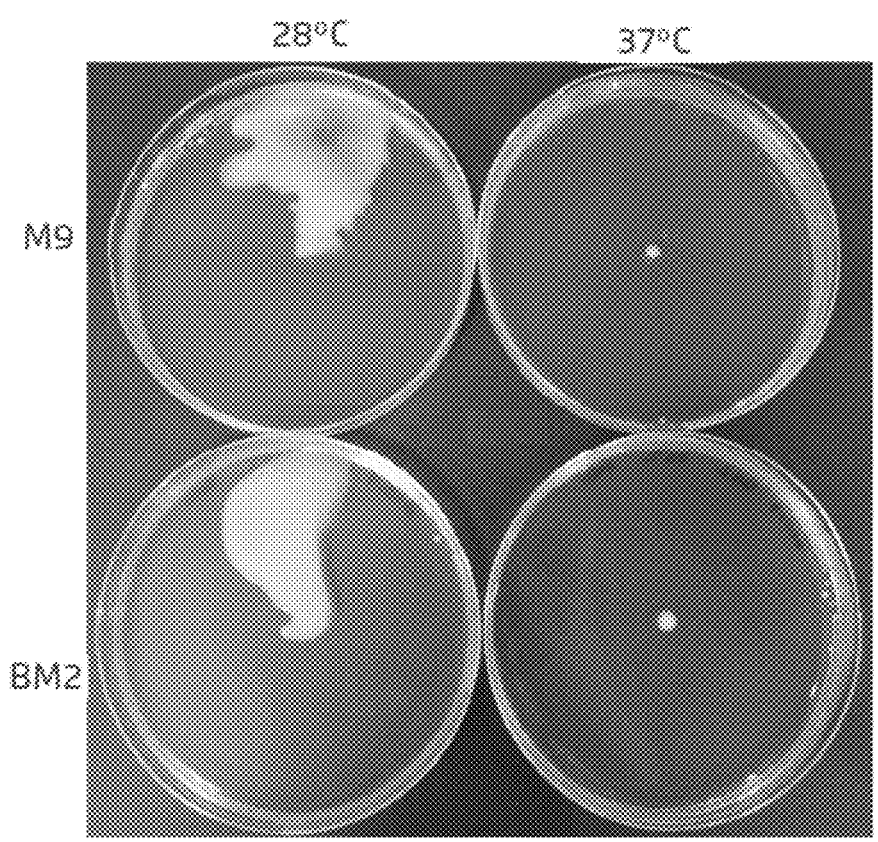
FIG. 1. CECT8538 has swarming capacity at 28° C. Representative images of *P. putida* CECT8538 incubated with M9 or BM2 at 28° C. (right) or 37° C. (left) for 30 h.

The colonization capacity is a crucial feature for biocontrol agents to adequately compete within the environment of the rhizosphere. To test this capacity of the strain of the invention, its bacterial swarming motility was assessed. Swarming is a specialized multicellular movement that facilitates the coordinated colonization of surfaces by bacteria. Briefly, a preculture of the strain of the invention was inoculated in plates containing either M9 or BM2 media, and incubated for 30 h at 28° C. or 37° C. (FIG. 1). As shown in FIG. 1 the strain of the invention has a high swarming capacity at 28° C., but not at 37° C. This indicates that the strain of the invention is metabolically active at 28° C., which is the soil average temperature, and it does not have it at 37° C., which is the optimal colonization temperature of human pathogenic microorganisms.

Example 3. Comparative Analysis of Cell Growth Capacity at Different pH

To compare the ability to survive at different pH within different *P. putida* strains, the strain of the invention, CECT8538, and the reference *P. putida* strains CECT324 and DSM6125 (KT2440) were pre-cultured on a shaker at 28° C. and 120 rpm overnight. These pre-cultures were seeded in NA petri plates with the desired adjusted pHs (see table 2), and incubated for 24 h at 28° C. pH adjustment was performed after sterilization of the NA medium, just before pouring the medium into the plates. Table 2 shows the results observed after 24 h of incubation. CECT8538 was the strain which was able to survive in a broader pH range when compared to the other *P. putida* strains, confirming the high adaptation capacity of the strain of the invention to the environment.

TABLE 2

Analysis of cell growth capacity of CECT8583 at different pHs.

| pH | 4 | 5 | 6 | 7 | 8 | 9 | 10 |
|---|---|---|---|---|---|---|---|
| CECT8538 | + | ++ | ++ | ++ | ++ | ++ | + |
| CECT324 | − | + | ++ | ++ | ++ | + | + |
| DSM6125 | − | ++ | ++ | ++ | ++ | + | + |

Example 4. Analysis of Antimicrobial Production by the Strain of the Invention

Example 4A. HPLC Analysis for Evidence of Metabolite Production by *P. putida* CECT8538

The most common antimicrobial metabolites produced by *Pseudomonas* spp. are pyrrolnitrin, 2,4-DAPG, pyoluteorin, and phenazines that play an important role in biocontrol. These metabolites can be synthesized by *Pseudomonas* spp. during the late logarithmic or stationary phase of growth.

In order to evaluate *P. putida* strain CECT8538 metabolites production, the strain of the invention was subject to a fermentation process to grow. Large scale cultivations were done in an industrial bioreactor F3-100 (F3-industrial model, Bionet) with a working volume of 100 litres, using LB culture medium, temperature adjusted at 28° C.±1° C., aeration of 8 L/min, Dissolved oxygen at >50% and stirred at 200-400 rpm. The culture was inoculated at 5% v/v with a preculture grown for 24 hours in a lab bioreactor F1-5 (F1-lab model, Bionet) under the same parameters of industrial bioreactor.

All parameters were controlled and measured during the fermentation (i.e. temperature, pH, oxygen pressure, agitation, airflow rate, foam level and optical density). Once fermentation was finished, the cells were harvested by centrifugation (Hitachi CR22N), the culture supernatant was stored at 4° C. and the cells were lyophilized (Heto Power Dry LL 3000) to conserve the biomass viability.

Potential metabolic fractions were analyzed by HPLC (eAlliance system, Waters). Chromatograms were performed using an XBridge C18 reversed-phase column (5 μm 4.6×150 mm, Waters) eluted (1 ml min$^{-1}$) with a linear gradient of 0-80% of acetonitrile in water for 15 min. Both solvents contained 0.05% trifluoroacetic acid (TFA). Metabolites were detected by UV spectroscopy with a photodiode array detector [for pyrrolnitrin, =247 nm and retention time ($t_r$)=14.6 min; for 2,4-DAPG, 2=278 nm and $t_r$=12.6 min; for pyoluteorin, 2=308 nm and $t_r$=10.6 min; for pyocyanin, 2=278 nm and $t_r$=5.5 min].

HPLC chromatograms of the different samples from the strain of the invention were compared with the chromatogram obtained for the standards metabolites pyrrolnitrin, 2,4-DAPG, pyoluteorin, and pyocyanin. The four peaks corresponding of each metabolite were absent in the chromatograms obtained from the strain of the invention.

Example 4B. Genomic Analysis to Determine the Ability to Synthesize Pyrrolnitrin, 2,4-DAPG, Pyoluteorin, and Pyocyanin Metabolites by the Strain of the Invention A complementary genomic study was performed to determine whether CECT8538 comprises the genetic machinery to synthesize these metabolites under other growth/storage particular conditions.

Firstly, the core biosynthetic pathways for each metabolite in *Pseudomonas* spp. were retrieved from the NCBI database. The homologues to pyrrolnitrin, 2,4-DAPG, pyoluteorin and pyocyanin biosynthetic enzymes were searched in the WGS of CECT8538, and protein-protein alignments were performed using BLASTp. A database consisting on the in silico translation of the genes predicted from the CECT8538 genome (5892 protein-coding genes) was obtained, using a bit score as cut-off parameter and applying a threshold of 40.

The pyrrolnitrin biosynthetic enzymes are encoded by genes located in the prn operon, which includes prnA (encoding a tryptophan halogenase), prnB (encoding a monodechloroaminopyrrolnitrin synthase), prnC (encoding an halogenase), and prnD (encoding an aminopyrrolnitrin oxygenase). *P. putida* strain CECT8538 has only a homologue of prnA from the prn operon, suggesting that CECT8538 is not able to synthetize pyrrolnitrin (Table 3).

The core biosynthetic pathway of 2,4-DAPG is encoded by genes in the phl locus, including phlA (encoding a β-ketoacyl-ACP synthase III), phlB (encoding a putative nucleic-acid binding enzyme), phlC (encoding a condensing enzyme), and phlD (encoding a type III polyketide synthase; PKS). Some PhlD proteins in *Pseudomonas* spp. showed a homologue in CECT8538, but no PhlA, PhlB or PhlC homologues were found in the strain of invention (Table 3). Thus, it is derived that CECT8538 is not able to synthetize 2,4-DAPG.

Pyoluteorin biosynthetic genes, in *P. fluorescens* Pf-5, are grouped in the plt gene cluster. This includes 10 genes although only 7 constitute the core pyoluteorin biosynthetic pathway: pltF (encoding a acyl-CoA synthase), pltE (encoding a acyl-CoA dedehydrogenase), pltA and pltM (both encoding halogenases), pltB (PKS), pltC (PKS) and pltG (thioesterase). From these 7 pyoluteorin biosynthetic proteins, PltF had a homologue in CECT8538; only in some species/strains PltA, PltB, PltC, PltE, and PltM showed homology with a CECT8538 protein; and no PltG had a homologue in the strain of invention. The thioesterase PltG is probably responsible for termination of polyketide assembly, thus the absence of pltG suggests that CECT8538 is not able to synthetize pyoluteorin.

Phenazines, such as phenazine-1-carboxylic acid (PCA) and pyocyanin, are virulence factors in *P. aeruginosa*. Both stimulate a neutrophilic inflammatory response and up-regulate chemokines (IL-8) and adhesion molecules (ICAM-1) by oxidant-dependent mechanisms. The biosynthesis of pyocyanin is achieved by the combined action of the core phenazine biosynthetic pathway leading to PCA, and pyocyanin-specific biosynthetic reactions that allow the conversion of PCA into pyocyanin. These two sets of reactions are catalyzed by enzymes encoded in two respective operons. Five genes of the phz gene cluster –phzB/A (encoding ketosteroid isomerase; phzA is a non functional copy of phzB), phzD (encoding isochorismatase), phzE (similar to anthranylate synthase), phzF (encoding a trans-2,3-dihydro-3-hydroxyanthranilate isomerase) and phzG (encoding a flavin-dependent oxidase)—are strictly necessary for the biosynthesis of PCA, the precursor of pyocyanin. In addition, the action of phzM and phzS, encoding the PCA methyltransferase and a flavin dependent hydroxylase respectively, are also strictly necessary for the biosynthesis of pyocyanin.

In the NCBI database there are thousands of PhzF sequences from *Pseudomonas* spp., from which 27 correspond to *P. putida*. CECT8538 has a PhzF copy homologue to those of other *P. putida* strains (Table 3), and the in silico translation of the genes predicted from the CECT8538 genome sequence predicts the presence of a phzF copy in this strain. Regarding accessions for PhzA, PhzB, and PhzD, searches were limited to accessions corresponding to *P. putida* and those corresponding to reference genes in *Pseudomonas* spp. (all belong to *P. aeruginosa*). The accession corresponding to *P. putida* NJ-10 PhzD showed a homologue in CECT8538, and the same was observed with PhzD proteins from *P. aeruginosa* PAO1. On the other hand, PhzA and PhzB did not show homologues in CECT8538, neither the sequences from *P. putida* FDAARGOS, nor those from *P. aeruginosa* PAO1.

No PhzE, PhzG, PhzM, and PhzS homologues were found in the NCBI database from any *P. putida* strain. However, CECT8538 showed a predicted protein homologue to *P. aeruginosa* PAO1 PhzE, and two CECT8538 proteins showed homology to 3 accessions found for PhzG in *Pseudomonas* spp. In addition, while none of the two reference phzM genes from *Pseudomonas* spp. (both belong to *P. aeruginosa*) had a homologue in CECT8538, the phzS reference gene (also from *P. aeruginosa*) had a homologue in the strain of the invention. Due to the lack of PhzB, a ketosteroid isomerase essential for the biosynthesis of the pyocyanin precursor PCA, and the lack of PhzM, a methyltransferase necessary for the biosynthesis of pyocyanin, it is deduced that CECT8538 is not able to synthesize pyocyanin.

All these data confirms what HPLC analysis revealed, and indicates that the strain of the invention is not able to produce some antimicrobial metabolites because of the lack of specific genes required for their synthesis. The inability to produce these toxins, which can account for problems of antibiotic resistance in human pathogens, confers to the strain of the invention a proper profile to be used to treat plants intended for human consumption.

TABLE 3

Homologues to pyrrolnitrin, 2,4-DAPG, pyoluteorin, and pyocyanin biosynthetic enzymes

| Metabolite | Biosynthetic protein | Homologues[a] | Conclusion |
|---|---|---|---|
| pyrrolnitrin | PrnA | 23/23 | Yes |
|  | PrnB | 0/17 | NO |
|  | PrnC | 0/280 | NO |
|  | PrnD | 0/14 | NO |
| 2,4-DAPG | PhlA | 0/14 | NO |
|  | PhlB | 0/25 | NO |
|  | PhlC | 0/250 | NO |
|  | PhlD | 7/128 | ? |
| Pyoluteorin | PltA | 1/3 | ? |
|  | PltB | 2/3 | ? |
|  | PltC | 2/3 | ? |
|  | PltE | 1/2 | ? |
|  | PltF | 2/2 | Yes |
|  | PltG | 0/2 | NO |
|  | PltM | 1/3 | ? |
| Pyocyanin[b] | PhzB/A | 0/4 | NO |
|  | PhzD | 1/1 (2/2) | Yes |
|  | PhzE | NF (2/2) | Yes |
|  | PhzF | 23/27 (NA) | Yes |
|  | PhzG | NF (2/3) | ? |
|  | PhzM | NF (0/2) | NO |
|  | PhzS | NF (1/1) | Yes |

[a]The numbers denote the number of sequences with a homologue in CECT8538 versus the number of *Pseudomonas* spp sequences searches.
[b]For pyocyanin, the numbers denote the number of sequences with a homologue in CECT8538 versus the number of *P. putida* sequences searches. In brackets, it is shown the number of sequences with a homologue in CECT8538 versus the number of reference genes from *Pseudomonas* spp.
[c]NF: Not found

Example 5. Industrial Scale Production of a Composition of the Invention

For industrial scale production of compositions with the strain of the invention, optimal fermentation conditions described below using a F3-100 type bioreactor in liquid medium can be used, although techniques based on solid media fermentation may also be used, all of them being standard methods used in the microbiological industry.

In order to determine the optimal conditions, a F1-F5 bioreactor was used with 10LLB medium at 28° C., pH 7.0, pO$_2$>50% ramp, and stirring at 200-400 rpm. An exponential culture of the *P. putida* CECT8538 was inoculated at 5% v/v and the operational parameters of the bioreactor were monitored, the growth ending in steady phase in 12 h and getting cellular concentrations of 2.0×10$^9$ CFU/mL. Then, the culture was centrifuged in Hitachi CR22N centrifuge at 5000 rpm and cells were collected aseptically. At the end of this step, the biomass was concentrated by resuspending in 500 ml buffer, obtaining about 1 litres of 2.0×10$^{10}$ CFU/mL concentrate. An inert osmotic protector ingredient (1 L) was added later to the concentrate and dehydrated in a Heto Power Dry LL 3000 lyophiliser under standard conditions for 72 h, obtaining about 100 g dry weight (50% active material), with a concentration of 1.0×10$^{11}$ CFU/g p.s. In such conditions a product with a cell viability close to 90%, stable, easy to store and handle is obtained, which at operational doses of 5×10$^7$ CFU/mL allows the preparation of about 200 L of a product ready to be applied on the crop plants to be protected. Subsequently, the material was packaged in vacuum sealed bags, and preserved at 4° C., which maintains its shelf life for more than one year.

Example 6. Biocontrol Activity of Strain CECT8538

Example 6A. Activity Assessment of the Strain of the Invention Against *Erwinia Carotova* Subsp. *Atroseptica* on Potato Crop Biobactericide activity was assessed by in-house Method of Analysis (MA 10 "Determination of biocide or biostatic activity in vivo", Futureco Bioscience).

Three independent bioassays were set up with potato tubers in order to assess the antagonistic activity of the BCA *Pseudomonas putida* strain CECT8538 against *Erwinia carotovora* subsp. *atroseptica* (strain DSM 30184, DSMZ German Collection, isolated from a potato plant) the causal agent of the bacterial disease known as "bacteria soft rot". For these tests, potato variety "Kennebec" was selected since it is one of the most common cultivated varieties in Spain. Three different compositions formulated as Technical Grade Active Ingredient (TGAI; consisting of freeze dried material composed of 50% w/w of viable cells and 50% w/w sucrose), wettable powder formulation (WP; composed of 10% w/w TGAI, 2% w/w precipitated silica (CAS 1343-98-2), 3% w/w Carboximetil cellulose (CAS 9004-32-4), 2% w/w Naphtalene and alkyl naphtalene sulphonic acid, sodium salt (CAS 68425-94-5), 0.5% w/w 2R)-3-(2-hydroxy-3-methoxyphenyl)-2-[2-methoxy-4-(3-sulfopropyl) phenoxy]propane-1-sulfonic acid (CAS 105859-97-0), and 82.5% w/w Bentonite (Montmorillonite type, CAS 1302-78-9)), and oil dispersible formulation (OD; composed of 10% w/w TGAI, 1% w/w precipitated silica (CAS 1343-98-2), 20% w/w Trimethylnonylpolyethylene glycol (CAS 60828-78-6), and 69% w/w linseed oil refined (CAS 68649-95-6)) were assessed.

Approximately 2×2 cm sprouted potato tubers were disinfected (commercial bleach 1.2%, 5 minutes and then 3 baths with distilled water), sowed and grown during four-five weeks on peat:vermiculite substrate (1:1; v/v) in growth chamber conditions (Fitoclima 20000, ARALAB; 18-20° C.; 60-70% RH, 13 h:11 h day:night; 270-300 PAR). After four-five weeks, seedlings were transferred into 1 L pot with soil:peat:perlite substrate (2:1:0.5; v/v). A randomized block design consisting of 3 replicates per treatment, with 4 plants per replicate (12 plants per treatment) was carried out. The testing substances (TGAI, WP or OD) were applied three times throughout each bioassay. First test application (A) was performed 24 h after transplant (6 days before pathogen challenge) by adding 20 mL containing different concentrations of the test substances on the substrate (see Table 4). Inoculation with the pathogen was performed 7 days after transplant by adding 20 mL of a pathogen bacterial suspension (2×10$^9$ CFU/mL; 4×10$^7$ CFU/plant) from a 24 h pre-culture per plant. Two more applications (B and C) with the strain of the invention were done one and two weeks after the first one at a rate of 20 mL per plant (B=7DAA; C=14 DAA; DAA means "days after A treatment". In the 3 bioassays, a control infected with the pathogen but not treated with the strain of the invention was included.

Plants were maintained in growth chamber conditions (Fitoclima 20000, ARALAB) during 4 weeks (20° C. (day), 18° C. (night); 60-70% HR; 13 h:11 h day:night; 270-300 PAR) and watered daily. Twenty two days after transplant to the 1 L pots, plants were rated for Bacteria Soft Rot disease Severity (Percentage of BSR as necrotic vascular lesion). Efficacy was assessed by measuring the percentage of damage stem as brown rot related to the total length of the stem 7 days after last application (7 DAC, days after C treatment).

The percentage of efficacy was calculated using Abbot's formula:

$$\text{Efficacy \%} = 100 - \frac{(TR \times 100)}{UNTR}$$

TR=percentage of damaged stem on the treated plot
UNTR=percentage of damaged stem on the untreated plot

TABLE 4

Efficacy against *Erwinia carotova* subsp. *atroseptica* on Potato plants cv Kennebec under controlled conditions

| ASSAY | TREATMENT | Concentration CFU/ml* | % SEVERITY | % EFFICACY/ SEVERITY |
|---|---|---|---|---|
| Exp 1 | Control | | 22% | |
| | TGAI | 1.26E+08 | 11% | 50% |
| Exp 2 | Control | | 57% | |
| | TGAI | 5.40E+07 | 40% | 30% |
| | WP | 4.43E+07 | 32% | 44% |
| Exp 3 | Control | | 41.40% | |
| | TGAI | 5.80E+06 | 31.50% | 24% |
| | OD | 2.70E+07 | 21.00% | 49% |

As shown in the table, the strain of the invention has the capability to colonize potato's crops and act as a biocontrol agent against the bacteria *Erwinia carotovora* subsp. *atroseptica*. These data show that the strain of the invention has the capacity to colonize an infected plant, and antagonize the diseases caused by a bacterial infection in it.

Example 6B. In Vitro Antifungal Activity of *Pseudomonas putida* Strain CECT8538

To assess the biocontrol capacity of the strain of the invention, its phytopathogenic capacity against fungi was tested in vitro using the poisoned food technique. For the evaluation, 8 fungi were selected, 4 strains acquired from a microorganism collection (*Botrytis aclada* CECT 2851, *Rhizoctonia solani* DSMZ 63010, *Pythium ultimum* CECT 20902, and *Sclerotinia sclerotiorum* CECT 2822), and 4 strains from Futureco Bioscience's culture collection isolated from infected plants (*Sclerotinia sclerotiorum* strain H24 isolated from lettuce, *Colletotrichum coccodes* strain H827 isolated from potato, *Fusarium oxysporum* strain H828 isolated from tomato, and *Alternaria porri* strain H830 isolated from onion).

As mentioned above, the fungal inhibition tests were performed against the indicated phytopathogens by the Poisoned Food technique. Briefly, bacterium was overnight cultured in LB medium at 28° C. and 200 rpm. From this stationary culture, a solution of the biocontrol agent CECT8538 was pipetted aseptically into temperate potato dextrose agar (PDA) to reach two final bacterial concentrations, $3 \times 10^6$ and $3 \times 10^7$ CFUs ml$^{-1}$. Then, the medium was poured into 9 cm Petri plates and, after solidification, agar discs (6 mm diameter) containing mycelium from the active growing edge of 7 days-old cultures of the pathogen strains were placed on the centre of each plate in an inverted position to achieve greater contact of the mycelium with the poisoned media. Each treatment was done by triplicate. Plates were incubated at 26° C. in the dark and the radial mycelial growth of fungal colony was followed by measurement of the shorter and longer radius at different days. The assay was repeated at least twice for each pathogen. The effect of CECT8538 in vitro was compared to control plates (PDA without the bacteria amendment).

The strain of the invention showed strong antagonistic activity against all the fungal pathogens tested (FIG. 2). Differences in growth area between fungi growing in PDA with bacterium and control (PDA alone) were observed after 3 days of incubation and this growth inhibition was better when the higher dosage of CECT8538 was used.

Example 6C. Comparative Analysis of *B. aclada* Antagonistic Activity Between Different *P. putida* Strains

*Botritys aclada* is one of the causal agents of onion neck rot, and the one responsible for the higher losses in terms of production. Although the symptoms related to *B. aclada* infection appear during onion storage, the infection takes place in the field. It is known that some *P. putida* strains, such as WCS3558 can inhibit other *Botrytis* species like *B. cinerea*, which affect other kind of fruits crops like grapes.

The inventors identified that the strain of invention has the capacity to inhibit *B. aclada* CECT 2851 growth (example 6B), but it was not clear if this capacity was specific of the strain of the invention or other *P. putida* strains could have the same effect. To assess that, a comparison analysis using the strain of the invention and the reference *P. putida* strains, CECT324 and DSM6125 (KT2440) was performed.

Figure 3:
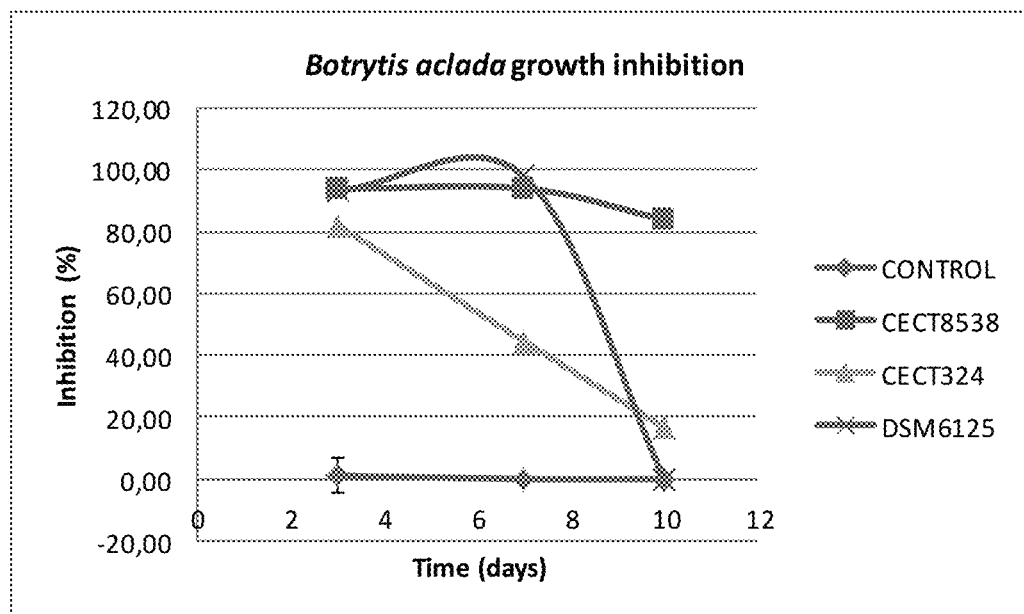
FIG. 3. Kinetics of fungal growth of *Botryis aclada* exposed or not to the indicated *P. putida* strains. The graph shows the % of growth inhibition of *B. aclada* growing in PDA (control; diamond), PDA inoculated with CECT8538 (square), PDA inoculated with CECT324 (triangle), and PDA inoculated with DSM6125 (crosses) at 3, 7 and 10 days after inoculation.

As described above, the growth inhibition capacity was measured by the poisoned food technique and fungal growth was monitored at 3, 7, and 10 days (see FIG. 3 and Table 5).

Table 5 shows the final results 10 days after *P. putida* strains inoculation. The strain of the invention was the unique *P. putida* strain which maintained a significant effect on *B. aclada* growth after 10 days of incubation. The reference strains also had the capacity to inhibit the growth of *B. aclada* 3 days after inoculation but they lose their effect at 7 and 10 days after inoculation (FIG. 3). Therefore, although the three tested strains had an inhibitory effect at the beginning of the assay, only the strain of the invention had a long lasting effect on *B. aclada*'s growth. Moreover, the amount of the strain of the invention was of the same order as the amount of the comparative strains, and the inhibitory effect obtained with the strain of the invention was remarkably improved.

TABLE 5

Comparative analysis of growth inhibition of *B. aclada* by the different tested *P. putida* strains.

| Concentration (ufc/mL) | Strain | Growth (%) | Inhibition (%) |
|---|---|---|---|
| $3.9 \times 10^7$ | CECT8538 | 16.01 | 83.99 |
| $1.2 \times 10^7$ | CECT324 | 83.35 | 16.65 |
| $2.79 \times 10^7$ | DSM6125 | 100 | 0 |

CITATION LIST

1. Mora et al., "Antimicrobial peptide genes in *Bacillus* strains from plant environments", International Microbiology, 2011, vol. 14, pp. 213-223

The invention claimed is:

1. A pesticide composition comprising a *Pseudomonas putida* strain deposited in the Spanish Type Culture Collection (CECT) with the accession number CECT8538 wherein the composition comprises from $3\times10^6$ to $1\times10^{11}$ colony forming units (CFU) of said *Pseudomonas putida* strain per mL of the composition and one or more osmotic protectors.

2. The pesticide composition of claim 1, wherein at least one osmotic protector is selected from trehalose, betains, and amino acids.

3. The pesticide composition of claim 2, wherein at least one osmotic protector is selected from betains.

4. The pesticide composition of claim 2, wherein at least one osmotic protector is selected from amino acids.

5. The pesticide composition of claim 1 which comprises an inoculation product.

6. The pesticide composition of claim 5 which further comprises one or more agriculturally acceptable compounds.

7. The pesticide composition of claim 6, wherein the one or more agriculturally acceptable compounds is selected from the group consisting of plant strengtheners, nutrients, wetting agents, compounds that improve adherence, buffering compounds, stabilisers, antioxidants, and sunscreens.

8. The pesticide composition of claim 6, comprising at least one additional pesticide.

9. The composition according to claim 8, wherein the additional pesticide is selected from the group consisting of a bacterial strain with antifungal, antibacterial activity, a fungicide, a bactericide, an herbicide, an insecticide, and a nematicide.

10. The pesticide composition as defined in claim 1, which further comprises one or more agriculturally acceptable compounds.

11. The pesticide composition according to claim 10, wherein the one or more agriculturally acceptable compounds is selected from the group consisting of plant strengtheners, nutrients, wetting agents, compounds that improve adherence, buffering compounds, stabilisers, antioxidants, and sunscreens.

12. The pesticide composition according to claim 10, comprising at least one additional pesticide.

13. The composition according to claim 12, wherein the additional pesticide is selected from the group consisting of a bacterial strain with antifungal, antibacterial activity, a fungicide, a bactericide, an herbicide, an insecticide, and a nematicide.

14. A process for obtaining a pesticide composition of claim 1, the composition comprising a viable cell suspension derived from the strain CECT8538 of *Pseudomonas putida* as defined in claim 1, the process comprising: (i) inoculating the strain in a culture medium, (ii) subjecting the inoculated culture medium of step (i) to conditions suitable for growth of the strain, (iii) optionally subjecting the medium resulting from step (ii) to a concentration step, and (iv) adding the one or more osmotic protectors to the composition.

15. A method for controlling an infection caused by bacterial or fungal pathogen in a plant, comprising applying the pesticide composition of claim 1 to the affected part of the plant and/or to the seed or to the substrate or soil used for growing said plant.

16. A method for controlling an infection caused by bacterial or fungal pathogen in a plant, comprising applying the pesticide composition as defined in claim 5 to the affected part of the plant and/or to the seed or to the substrate or soil used for growing said plant.

* * * * *

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
agtttgatcc tggctcag                                                        18

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
acggttacct tgttacgact t                                                    21

<210> SEQ ID NO 3
<211> LENGTH: 953
<212> TYPE: DNA
<213> ORGANISM: Pseudomonas putida

<400> SEQUENCE: 3
tgcaagtcga gcggatgacg ggagcttgct ccttgattca gcggcggacg ggtgagtaat        60
gcctaggaat ctgcctggta gtgggggaca cgtttcgaa aggaacgcta ataccgcata       120
cgtcctacgg gagaaagcag gggaccttcg ggccttgcgc tatcagatga gcctaggtcg       180
gattagctag ttggtggggt aatggctcac caaggcgacg atccgtaact ggtctgagag       240
gatgatcagt cacactggaa ctgagacacg gtccagactc ctacgggagg cagcagtggg       300
gaatattgga caatgggcga aagcctgatc cagccatgcc gcgtgtgtga agaaggtctt       360
cggattgtaa agcactttaa gttgggagga agggcagtaa gctaatacct tgctgttttg       420
acgttaccga cagaataagc accggctaac tctgtgccag cagccgcggt aatacagagg       480
gtgcaagcgt taatcggaat tactgggcgt aaagcgcgcg taggtggttt gttaagttgg       540
atgtgaaagc cccgggctca acctgggaac tgcatccaaa actggcaagc tagagtacgg       600
tagagggtgg tggaatttcc tgtgtagcgg tgaaatgcgt agatataga aggaacacca       660 gtggcgaagg cgaccacctg gactgatact gacactgagg tgcgaaagcg tggggagcaa       720
acaggattag ataccctggt agtccacgcc gtaaacgatg tcaactagcc gttggaatcc       780
ttgagatttt agtggcgcag ctaacgcatt aagttgaccg cctggggagt acggccgcaa       840
ggttaaaact caaatgaatt gacggggccc cgcacaagcg gtggagcatg tggtttaatt       900
cgaagcaacg cgaagaacct taccaggcct tgacatgcag agaactttcc aga             953

<210> SEQ ID NO 4
<211> LENGTH: 1983
<212> TYPE: DNA
<213> ORGANISM: Pseudomonas putida

<400> SEQUENCE: 4
atggccgggc tgattcccca gagtttcatt gacgacctga tcaaccgcct cgacatcgtc        60
gacgtggtga gttcgcgcgt ccagctgaaa aaaccggca agaactactc ggcctgctgc       120
ccgttccaca agaaaaaaac cccgtccttc acggtcagcc ccgacaagca gttctactac       180

```
tgcttcggct gtggcgccgg tggcaacgcc ttgggctttg tcatggacca cgacaacctg      240
gacttccccc aggccgtcga ggaactggca cgcgccgctg gcatggaagt cccccgcgag      300
caaggccgcc gcgaccagaa gccgcgccag cccactgact cgccactgta cccgctactg      360
gacgccgcct cggagtttta ccgccaggcc ctgcgcagcc acccgtcacg caaggcagcg      420
gtggactacc tcaagggccg cggcctgtcc ggggaaattg cccgcgactt cggcctgggc      480
tttgccccgc ccggctggga caacctgctc aagcacctgg gtgccgacac cctgcagcag      540
aaggtgatga tcgatgccgg cctgctgatc gagaacgccg agagcggcaa cgctacgac       600 cgcttccgcg accgggtgat gttcccgata cgtgacagcc gcgggcgcat catcgccttc      660
ggtggccggg tgctcggcga cgacaagccc aagtacctga actccccgga accccggtg      720 ttccacaagg acaggagct gtacgggctg tacgaggcgc gcaagcacaa ccgcaacctc      780
gacgagatca tcgtcgtcga gggctacatg gacgtcattg ccctggccca gcaaggcctg      840
cgcaatgccg tggccaccct tggcaccgcc accagcgaag agcacctcaa gcgcctgttc      900
cgcgtggtgc ccagcgtgct gttctgtttt gacggtgacc aggctgggcg caaggcggcc      960
tggcgcgcac tggaatcgac attgtcgaac ctgcaggacg gccgtcgcgc gcgcttcctg     1020
ttcctgcccg aaggcgaaga cccggacagc ctggtgcgtg ccgaaggtac cgacgccttc     1080
atggcccgta tcaaccagca cgcccaaccg ctggccgact acttcttcga gcaacttggc     1140
gtcgaagccg acccgcgctc actggaaggc aaggcgcata tggcgacctt ggccgcaccg     1200
ttgatcgaaa agatccccgg cgccaacctg cgtcagctga tgcgcaaccg cctgaaggaa     1260
atcaccggcc tcgacccgca gcaggtcgag cagttggcgc agcaagcgcc ggcgaccagc     1320
agcatgccgg actacgaccc tggctacgat tacgacgcca tggccagcta caccccccgac     1380 tatgcgacga tgccgcagca cgactatgcc cccgttcatc aggagcaggc atggaaaccc     1440
aacaaggggg gcagcaagaa gccgtggagc gacaaaccct gggataagaa ccgcaagggc     1500
ggtaagccct ggcagcaacg cgacgaagca cctccccgcg tgccagcacc ggtcgagccg     1560 cccacccctgg ccgccctgcg caccctgctg caccaccac tgctggccgg caaggtggaa     1620
gatgccagcc acttcgccga cgaagaacac ctgtacagcc agctgctggt ggcactgatc     1680
gaagccgcgc agaaaaatcc tgggctaagc tcaatgcagt tgatcgcacg ttggcatggc     1740
accgaacagg gccgcctgct acgggccctg gcggaaaagg aatggcttat cgtgccgac      1800 aaccttgaac aacagttttt cgacactata actagcttgt ccgcccgcca acgcgagcgc     1860
agcctggaac aactgctcag gaaatcacgt caaagcgaat tgaccagcga ggaaaaaacc     1920
cagctcctcg ccctgctgag ccgaaatgtt cccgcacaaa cgccgacctc atctggcgcg     1980
tga                                                                   1983
```

<210> SEQ ID NO 5
<211> LENGTH: 639
<212> TYPE: DNA
<213> ORGANISM: Pseudomonas putida

<400> SEQUENCE: 5

```
atgacagtac gaaggtggt cacgcggcgg tccaaccatt accgcggcta cttcccatcg       60
ctcaaaaata aaaagcctgt gccctgggag tcccagctcg aaggcgctct ttttcggctt      120
cttgagctgt ctcctgcggt catcggctac gtcccgcagc ccagtgagga acgtgttcca     180
tcgctccagg gctacttcaa atattaccca gacgtacagg ttttcctcgc ggatgggcgc     240
gagtggtggt ttgaagtgaa gcctcacgac cgactgaaga ttgccagcgt caggcagcga     300
```

-continued

```
ctggatgccg ctgagcgcta cttcaacgcc actgcccgta acttttcggt gatcactgaa    360
aagttaattg aagctgaacc cctggctacc aatcttagaa ggctgatgta tcaccggcgc    420
ggtccagagc tttcgcatca ggcgttggag gaggtaatgg cgaccttcaa cgaatggccg    480
cctatgaccg ttgcagatct gctctacgtg gttggtgagg ggaaagcctg gcgcttgtta    540
ggccttgggg tggtgggcat tgaccttgat aggtcaattg acactgactc cccggtcttc    600
ctgcaagggg ggcaccgtca tgcaaacctt ttcccttag                           639
```